(12) United States Patent
Jansen et al.

(10) Patent No.: US 8,318,106 B2
(45) Date of Patent: Nov. 27, 2012

(54) ANALYSIS SYSTEM FOR ANALYZING A SAMPLE ON A TEST ELEMENT

(75) Inventors: Paul Jansen, Mannhein (DE); Jochen Schulat, Mannheim (DE); Yvonne Ringelspacher, Waldsee (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 973 days.

(21) Appl. No.: 11/189,668

(22) Filed: Jul. 26, 2005

(65) Prior Publication Data
US 2006/0024203 A1  Feb. 2, 2006

(30) Foreign Application Priority Data

Jul. 28, 2004  (DE) .................... 10 2004 036 474

(51) Int. Cl.
*G01N 21/75* (2006.01)
*G01N 31/22* (2006.01)
*G01N 33/52* (2006.01)
*G01N 21/00* (2006.01)

(52) U.S. Cl. ..................... 422/401; 422/82.05
(58) Field of Classification Search .............. 422/56
See application file for complete search history.

(56) References Cited

U.S. PATENT DOCUMENTS

| | | | |
|---|---|---|---|
| 5,104,619 A | 4/1992 | de Castro et al. | |
| 5,232,668 A | 8/1993 | Grant et al. | |
| 5,424,035 A * | 6/1995 | Hones et al. | 422/55 |
| 5,728,352 A * | 3/1998 | Poto et al. | 422/82.05 |
| 5,795,543 A | 8/1998 | Poto et al. | |
| 5,846,837 A | 12/1998 | Thym et al. | |
| 6,036,919 A | 3/2000 | Thym et al. | |
| 6,378,702 B1 * | 4/2002 | Kintzig | 206/456 |
| 6,475,436 B1 | 11/2002 | Schabbach et al. | |
| 6,881,378 B1 | 4/2005 | Zimmer et al. | |
| 7,240,565 B2 | 7/2007 | Eisenmann et al. | |
| 7,327,451 B2 * | 2/2008 | Markart | 356/244 |

(Continued)

FOREIGN PATENT DOCUMENTS

CA  2311496  6/1999

(Continued)

OTHER PUBLICATIONS

EP Search Report fro co-pending application EP05016248.6.

*Primary Examiner* — In Suk Bullock
*Assistant Examiner* — Bryan Kilpatrick
(74) *Attorney, Agent, or Firm* — Bose McKinney & Evans LLP

(57) ABSTRACT

The invention relates to an analysis system for analyzing a sample on a test element. The system has an analysis unit for generating a signal as a function of an analyte contained in a sample, and a detection unit for detecting the signal. The analysis system further includes a test element holder into which the test element can be reversibly introduced and in which it can be positioned relative to the analysis unit and the detection unit. The test element contains at least one guide element, which is suitable for laterally guiding the test element, so that the test element in the test element holder is held and guided only on an outer region of the test element, and an inner region of the test element introduced into the test element holder remains free. The test element contains a sample application site in the inner region.

36 Claims, 6 Drawing Sheets

U.S. PATENT DOCUMENTS

| | | |
|---|---|---|
| 7,510,682 B2 | 3/2009 | Frank et al. |
| 2002/0167668 A1 | 11/2002 | Voelkel |

FOREIGN PATENT DOCUMENTS

| | | |
|---|---|---|
| DE | 24 46 968 A1 | 4/1976 |
| DE | 196 11 347 A1 | 9/1997 |
| DE | A 197 53 847 | 6/1999 |
| DE | 19781162 C2 | 11/1999 |
| DE | 199 02 601 | 7/2000 |
| DE | 199 02 601 A1 | 7/2000 |
| DE | 199 12 365 | 9/2000 |
| DE | 103 49 914 A1 | 5/2004 |
| DE | 10 2004 022 757 A1 | 12/2005 |
| EP | A 0 821 233 | 1/1998 |
| EP | A 0 821 234 | 1/1998 |
| EP | 1 033 569 A1 | 9/2000 |
| EP | 1382968 B1 | 1/2004 |
| JP | 61013160 A | 1/1986 |
| WO | WO 96/15439 A1 | 5/1996 |
| WO | WO 97/02487 | 1/1997 |
| WO | WO 97/36168 A1 | 10/1997 |
| WO | WO 99/29429 | 6/1999 |
| WO | WO 00/19185 | 4/2000 |

\* cited by examiner

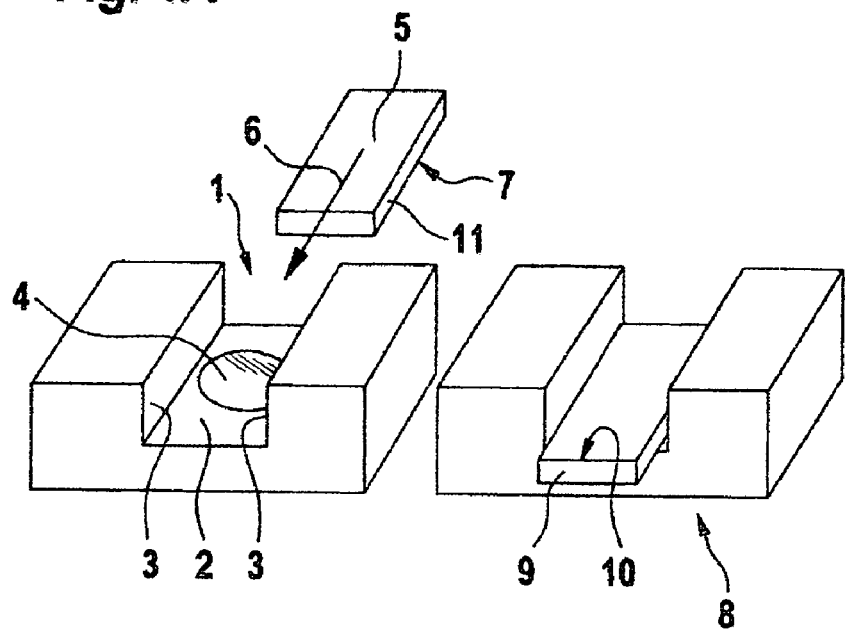
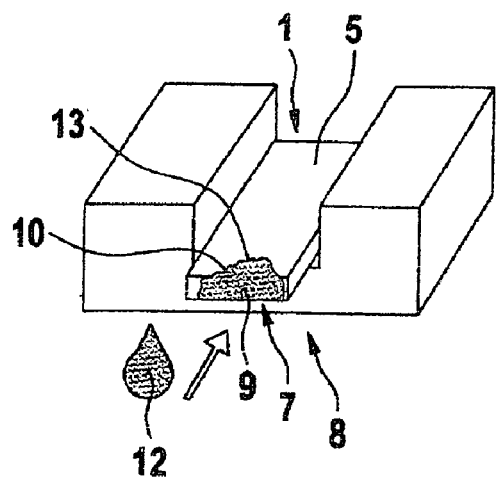
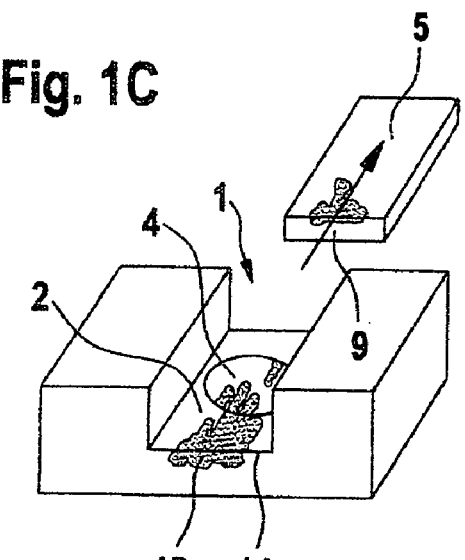
Fig. 1A
Fig. 1B
Fig. 1C

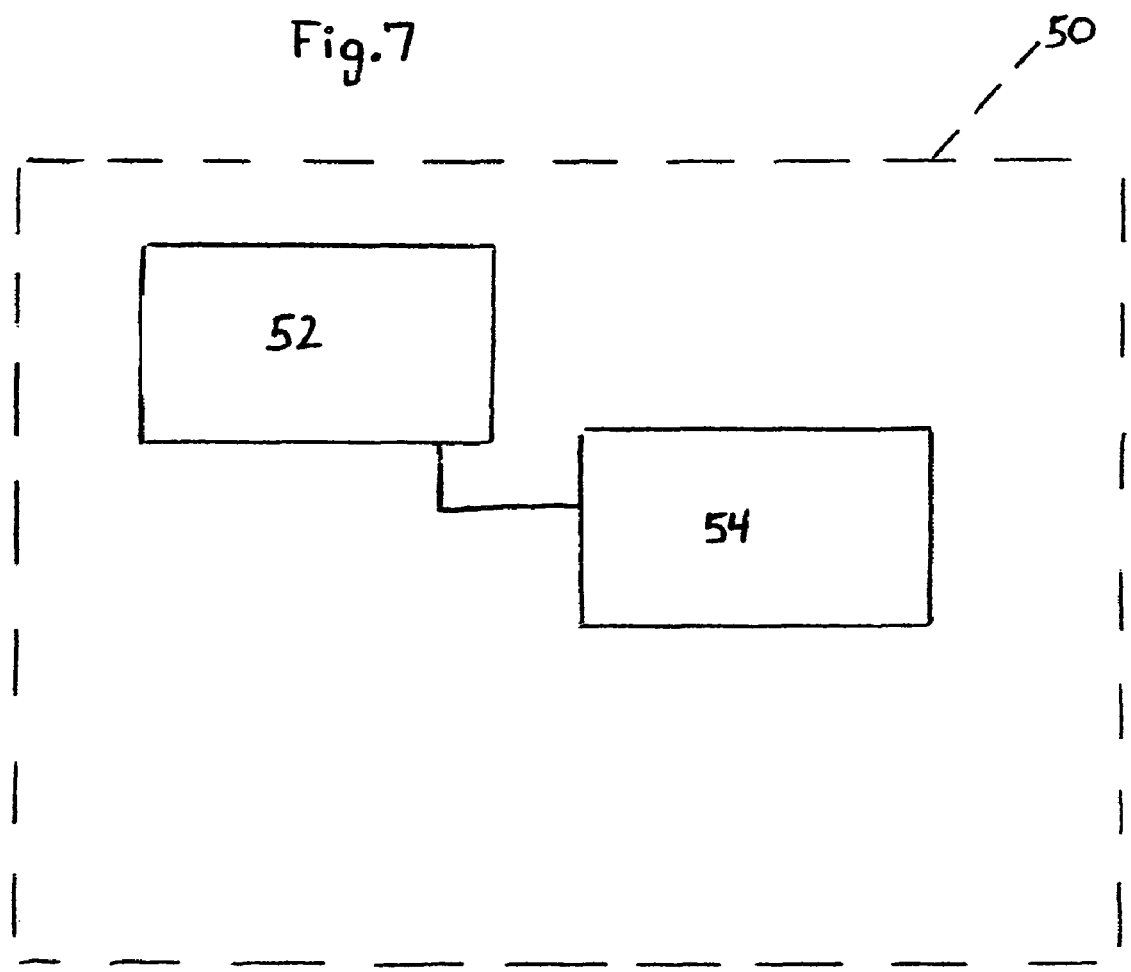

ANALYSIS SYSTEM FOR ANALYZING A SAMPLE ON A TEST ELEMENT

The present application claims priority to German Patent Application No. 10 2004 036 474.5, filed on Jul. 28, 2004, which is hereby incorporated by reference in its entirety.

TECHNICAL FIELD

The present invention relates to an analysis system for analyzing a sample on a test element.

BACKGROUND

In order to analyse samples, for example bodily fluids such as blood or urine, it is common to use analysis systems in which the samples to be analyzed are located on a test element, and optionally interact in a test field with one or more reagents on the test element before they are analyzed. The optical, in particular photometric, evaluation of test elements is one of the most commonly used methods for rapidly determining the concentration of analytes in samples. Photometric evaluations are widely used in the field of analysis, environmental analysis and above all in the field of medical diagnosis. Especially in the field of blood glucose diagnosis from capillary blood, test elements which are photometrically evaluated are of great value.

There are various forms of test elements. Essentially square sheets, also referred to as slides, in the middle of which there is a multilayer test field are known, for example. Diagnostic test elements which are of strip-shaped design are referred to as test strips. Test elements are described in the prior art, for example in the documents DE-A 197 53 847, EP-A 0 821 233, EP-A 0 821 234 or WO 97/02487. The present invention relates to test elements of any shape, and in particular strip-shaped elements.

Test elements in which a sample is applied to a sample application site, and is transported by means of capillary action to a detection zone (test field) separate from the sample application site, are known in the prior art. For example, DE 197 53 847 A1, published in English as CA2311496, which is hereby incorporated by reference in its entirety relates to such a test element. It describes an analytical test element for the determination of an analyte in a liquid. It contains an inert support, a detection element and a channel suitable for capillary liquid transport, which has a sample application opening at one end and a ventilation opening at the other end of the channel suitable for capillary liquid transport. The channel suitable for capillary liquid transport is formed at least partially by the support and the detection element, and extends in the capillary transport direction from the sample application opening at least as far as the detection element edge closest to the ventilation opening, a recess in a face which forms the channel suitable for capillary liquid transport being located on the test element edge forming the sample application element. The test element edge forming the sample application opening is thus interrupted at least partially on one side, and the face opposite the recess is free. The recess in a face forming the capillary channel on the edge of the test element is used to ensure that the sample liquid can enter the capillary channel. This is achieved in that the sample drop on the test element edge closest to the sample application opening, which is interrupted by the recess, can be brought directly in contact with one of the faces which form the inner surface of the capillary in their extension. By suitable choice of the geometry and dimensions of the recess, the liquid drop is very likely to come in contact with the active capillary zone and be readily sucked into the interior of the capillary, regardless of the exact position of the dosing.

For the analytical study of a sample on a test element, test element analysis systems are known in the prior art which contain a test element to position the test element in a measuring position, and a measurement and evaluation device for carrying out a measurement and determining an analysis result based on this. WO 00/19185 A1, which is hereby incorporated by reference in its entirety, relates to a device for the photometric evaluation of test elements, containing an illumination unit having at least a first light source and a second light source,
a frame for receiving a test element with a detection zone, so that the detection zone is positioned opposite the illumination unit,
a detection unit having at least one detector, which detects light reflected by the detection zone or transmitted through the detection zone,
a control unit, which activates the two light sources and records the signal generated by the detection unit as a detection signal, and
an evaluation unit, which evaluates the detection signals in order to determine the analyte concentration contained in the sample.

Known types of measuring apparatus have an opening, generally a slot, into which the test elements can be inserted. Guide elements ensure that a test element is inserted with the intended orientation. If the test element is introduced manually into the apparatus, design features of the apparatus must be provided which guarantee the desired positioning of the test element. This is usually done by a restriction which prevents insertion beyond a predetermined target position. Analysis systems which contain a storage container (magazine) with a multiplicity of test elements are furthermore known in the prior art. In this case, for example, a test element is transported from the storage container to the measuring position by a slide or plunger, and is automatically discarded from the analysis system after the measurement has been carried out.

DE 199 02 601 A1, published in English as U.S. Pat. No. 6,475,436 (B1), discloses a device for extracting a consumable analytical medium, in particular a test element, from a storage container which has one or more chambers containing consumable media. The chambers respectively have an extraction opening for extracting a consumable medium and an insertion opening, opposite the extraction opening, for introducing a plunger to transport the consumable medium. The extraction opening and the insertion opening are closed by a film in order to store the consumable medium. The device comprises a plunger which can be moved by means of a drive unit in order to extract a consumable medium.

Discarding the consumable test elements entails a contamination or infection risk since they are released without control into the environment and carry the rest of the sample material (for example blood, urine or interstitial fluid) on their surface. Hygienic handling and disposal of the test elements could be ensured by transport back into a storage magazine contained in the analysis system being used (re-magazining) or transport into a waste magazine intended for disposal of the test elements.

In the test element analysis systems known in the prior art, the test element in the measuring position rests via at least a large fraction of its lower side on a measuring apparatus surface in the analysis system. The lower side is pushed over the measuring apparatus surface during transport of the test element into and out of the measuring position. The test element is in this case guided by means of lateral guide faces which are perpendicular to the measuring apparatus surface. In a system for photometrically evaluating the test element, the measuring apparatus surface usually contains an optical window, below which the optics are located. Resting the test element via a large fraction of its lower side on the measuring apparatus surface has the disadvantage that a liquid sample applied to the test element, in the vicinity of one of its side edges, can stain the measuring apparatus surface. For example, a part of the liquid sample could be drawn by capillary forces between the test element and the measuring apparatus surface, so that a further region including the optical window is wetted with the sample. Such staining occurs in particular when the test element is being drawn back over the measuring apparatus surface into the magazine after the measurement has been carried out (re-magazining). In this case, any sample adhering to the test element edge used for the sample application will be wiped over the measuring apparatus surface.

The optical window of the analysis systems known in the prior art has to be sunk into the measuring apparatus surface in order to protect it against damage due to friction by the test element.

SUMMARY

The analysis system of the present invention comprises an analysis unit for generating a signal as a function of an analyte contained in a sample, and a detection unit for detecting the signal, and a test element holder into which the test element can be reversibly introduced and in which it can be positioned relative to the analysis unit and the detection unit. The test element contains at least one guide element which is suitable for laterally guiding the test element, so that the test element in the test element holder is held and guided only on an outer region of the test element, and an inner region of the test element introduced into the test element holder remains free. The test element contains a sample application site in the inner region.

Further, a method of analyzing the glucose content in a sample is provided in accordance with the invention. The method comprises the steps of providing a test element having an outer region and an inner region, the inner region containing a sample application site, providing an analysis system comprising an analysis unit for generating a signal as a function of glucose contained in the sample, a detection unit for detecting the signal, and a test element holder into which the test element can be reversibly introduced and in which the test element can be positioned relative to the analysis unit and the detection unit, the test element holder containing at least one guide element which is suitable for laterally guiding the test element, so that the test element in the test element holder is held and guided only on the outer region of the test element, and the inner region of the test element introduced into the test element holder remains free, applying a sample to the sample application site of test element, introducing the test strip into the test element holder so that the test element is held on the outer region, generating a signal as a function of the glucose contained in the sample, and detecting the signal.

Still further, an apparatus for holding a test element used in an analysis system is provided. The test element has an outer region and an inner region, the inner region containing a sample application site. The apparatus comprises a body being formed to include a guide element sized for laterally guiding the test element so that the test element in the body is held and guided only on the outer region of the test element, and the inner region of the test element introduced into the test element holder remains free, the guide element including spaced-apart support faces, on which the test element rests in its outer regions, and an optical window spaced-apart from the guide element.

In an embodiment of the invention, the analysis unit and the detection unit can be parts of measuring optics, which are used to photometrically evaluate the test element. A light source and optics are for example used as the analysis unit for photoelectric evaluation, and for example a photodetector which detects the light reflected by the test field supplied with the sample or transmitted through the test field (optical signal) is used as the detection unit. Such a detection signal is evaluated in the known way in order to determine the analyte concentration.

In an embodiment of the present invention, the guide element contains support faces, on which the test element rests via bearing faces in its outer region, and guide faces along which side faces of the test element are guided. In this context, care should be taken that sufficient clearance still remains between the slue faces of the test element and the guide faces, so that the test element can be moved in the guide element with minimal force exertion and so as to maintain a low level of wear (for example, abrasion of the test element or notching in the guide walls).

In an embodiment of the present invention, the guide faces are arranged obliquely with respect to the side faces of the test element. The effect achieved by this is that a test element does not touch the guide faces over the entire side faces when it is being introduced into the guide element, but is displaced along the guide faces via one edge. This is particularly for test elements which are made of different layers adhesively bonded together. Such a test element is described, for example, in DE 199 12 365 A1 published in English as U.S. Pat. No. 6,881,378 (B1), which is hereby incorporated by reference in its entirety. Because of the obliquity of the guide faces, they are not stained by any adhesive which may be encountered on the side faces of the test element.

The bearing faces on which the test element rests in its outer region have a width of from 0.1 mm to 1 mm, particularly from 0.3 mm to 0.5 mm. With a correspondingly small clearance, they are therefore wide enough to prevent the test element from undesirably falling out of the guide element.

In an embodiment of the present invention, the guide element contains two mutually opposite grooves, into which the test element can be inserted via its outer region. In such a guide element, the test element is introduced by a sliding movement into two grooves, one each on the left-hand and right-hand sides of the test element. The grooves enclose the edges and side faces of the test element so that the test element cannot fall out of the guide element neither upwards nor downwards (closed guiding).

In an embodiment of the present invention, the guide element is arranged above the analysis unit and/or the detection unit in the analysis system. For the photometric evaluation, for example, the measuring optics (including the light source and photodetector) are arranged at a slight distance below the guide element in the analysis system. It is nevertheless possible to arrange the analysis unit above the guide element and the detection unit below the guide element, or vice versa.

In an embodiment of an analysis system according to the invention, the guide element is arranged so that a test element introduced into the guide element is at a distance of at least 1 mm from the analysis unit and the detection unit in any position. This distance ensures that the liquid sample cannot be drawn in by capillary forces between the test element and the analysis unit or the detection unit, and stain it. Furthermore, for example, an optical window no longer has to be sunk into the measuring apparatus surface since the distance protects it from mechanical stress, which simplifies the design of the analysis system.

In an embodiment of the present invention, the test element holder contains a stop, against which a test element abuts when it is being introduced into the guide element, so that a defined position of the test element in the test element holder is achieved. The stop establishes how far the test element should be introduced into the guide element.

In an embodiment of the present invention, the test element comprises a sample application site at one end in the inner region, the test element being tapered in the region of the sample application site. The tapering may, for example, be in the form of a shoulder or indentation. This test element can be wetted with the sample only over the width of the tapered end in its inner region, and not over the full width. The outer region of the test element, in which it is held and guided, thus remains free of the sample, and staining of the guide element which is in contact with the outer region is substantially avoided. The tapered region of the test element, with the sample application site, may furthermore protrude out of the test element holder in order to allow sample application on the outside. In particular, the guide element may have a stop on which the wide (normal) region of the test element, which is next to the tapered region, abuts as soon as it has been introduced over a sufficient distance into the guide element.

In an embodiment of the present invention, the analysis system also comprises a storage container for a multiplicity of test elements, into which the test elements are transported back from the test element holder after use. As such, the used test elements are handled and disposed of hygienically. The analysis system according to the invention in this case has a transport device for automatically extracting a test element from the storage container, for automatically transporting the test element into the test element holder and for automatically transporting the test element back into the storage container after use. The transport device comprises, for example, a plunger, a hook or a clip, which can couple to a test element and subsequently transport it into a desired position in the analysis system. In an embodiment of the present invention, the test element has a test field where the sample is analyzed, and which is positioned in the inner region of the test element. For the qualitative or quantitative analytical determination of components of the liquid sample, in particular bodily fluids, reagents are embedded in the test field. The test field is brought in contact with the sample and, if a target analyte is present, the reaction between the liquid sample and the reagents leads to a detectable signal, for example a colour change, which can be detected with the aid of the analysis unit and the detection unit. In the present invention, the test element contains a capillary for delivering the sample to the test field.

In one embodiment of the present invention, the test element holder is made of at least two parts, with a test element introduced into the test element holder resting in its outer region on a lower part of the test element holder and with a separate upper part of the test element holder resting on the test element in its outer region. In the absence of a test element, the two parts are placed loosely on one another and are laterally secured against displacement. When a test element is introduced into the guide element between the two parts of the test element holder, the two parts are pressed apart from each other by the test element. The test element therefore fits tightly into the guide element and is held in position by the upper part, which rests on its outer region, for example when the sample application and/or measuring position has been reached.

At least one pressure spring, which exerts a force on the upper part in the direction of the lower part of the test element holder, is arranged on the upper part of the test element holder. The spring force additionally holds the test element in position.

In the present invention, the guide element may have a ramp- or funnel-shaped introduction opening on the side where a test element is introduced into the test element holder. The ramp- or funnel-shaped introduction opening facilitates the introduction of a test element into the guide element.

In one embodiment of the present invention, the guide element is shaped so that it causes a defined deformation of a test element introduced into the test element holder, in order to fix it during use. For example, the guide element may be bent in the longitudinal direction so that a test element is deformed in a defined way in the longitudinal direction when it is being introduced into the guide element, and is under a flexural stress in the measuring position. This ensures the defined distance of the test field from the measurement unit comprising the analysis unit and the detection unit. Likewise, for example, the guide element designed as two grooves may be inclined with respect to the introduction plane of the test element so that the test element in the guide element is deformed in a defined way in the transverse direction. This likewise fixes the test element in the test element holder.

These and other features of the present invention will be more fully understood from the following detailed description of the invention taken together with the accompanying claims. It is noted that the scope of the claims is defined by the recitations therein and not by the specific discussion of the features set forth in the present description.

BRIEF DESCRIPTION OF THE DRAWINGS

The invention will be explained in more detail below with reference to the drawings, in which:

FIG. 1A shows the introduction of a test element into a guide element of an analysis system in the prior art, FIG. 1B shows the sample application on a test element in a guide element of an analysis system in the prior art, FIG. 1C shows the extraction of a test element after a measurement from a guide element of an analysis system in the prior art.

FIG. 7 shows the schematic representation of a detail of an analysis system according to the invention, into which a test element is introduced, and a diagrammatic view of an analysis unit and a detection unit that are parts of measuring optics which are used to photometrically evaluate the test element.

DETAILED DESCRIPTION OF THE DRAWINGS

Figure 2A:
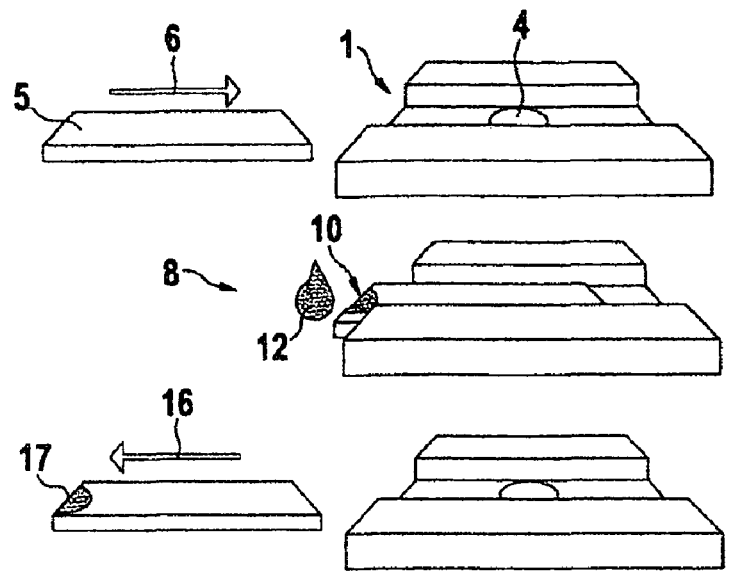
FIG. 2A shows the manual handling procedure for a test element in an analysis system of the prior art.

FIG. 1A schematically shows the introduction of a test element into a guide element of an analysis system in the prior art.

In this case, the guide element 1 is a sort of open trough with a bearing face 2 and side walls 3. In the bearing face 2, there is an optical window 4 (symbolized by the circle) below which measuring optics (not shown) are arranged for photometrically evaluating the test element 5. A test element 5 is introduced into the guide element 1 in the introduction direction 6, while sliding with its full width via its lower side 7 over the bearing face 2. It is guided during introduction by the side walls 3, along which the side faces 11 of the test element 5 slide. In the sample application position 8, the test element 5 rests extensively on the bearing face 2. The test element 5 protrudes beyond the bearing face 2 via its end 9, which contains the sample application site 10.

This design of the guide element 1 as represented in FIG. 1A, in which the test element 5 guided only laterally rests flat via the lower side 7, is configured so that after the measurement (and the sample application associated with it) the test element is not guided through the guide element 1 via the end to which the sample has been applied. This movement does, however, take place in an analysis system with a re-magazining function. This will be demonstrated in FIGS. 1B and 1C.

FIG. 1B shows the sample application on a test element in a guide element of an analysis system in the prior art.

The test element 5 is displaced into the sample application position 8 while being guided by the guide element 1, as represented in FIG. 1A. In order to apply the sample 12, for example blood, the test element 5 protrudes slightly from the analysis system in this position. A sample 12 is applied onto the test element 5 at the sample application site 10. For this, the end 9 of the test element 5 is dipped slightly into the sample 12 so that it is wetted with the liquid sample 12 on its upper side 13 and its lower side 7.

FIG. 1C shows the extraction of a test element after a measurement from a guide element of an analysis system in the prior art.

If, after the measurement, the test element 5 is drawn back counter to the introduction direction 6 (for example to re-magazine the test element 5) from the sample application position 8 through the guide element 1, then drops of the sample 12 adhering to the end 9 of the test element 5 will be wiped off on the edge 14 of the guide element 1. By capillary forces, sample material will be drawn into the gap between the test element 5 and the bearing face 2, and will be further distributed over the bearing face 2 by the extraction of the test element 5 over it. This leads to contamination or staining 15 of a wide region of the bearing face 2, including the optical window 4, by the sample material. The optical window 4 of the guide element 1 of an analysis system in the prior art, as shown in FIGS. 1A to 1C, needs to be sunk into the bearing face 2 for the test element 5, in order to protect it against damage due to friction by the test element 5 during the introduction and the extraction of the test element 5 from the guide element 1.

Figure 2B:
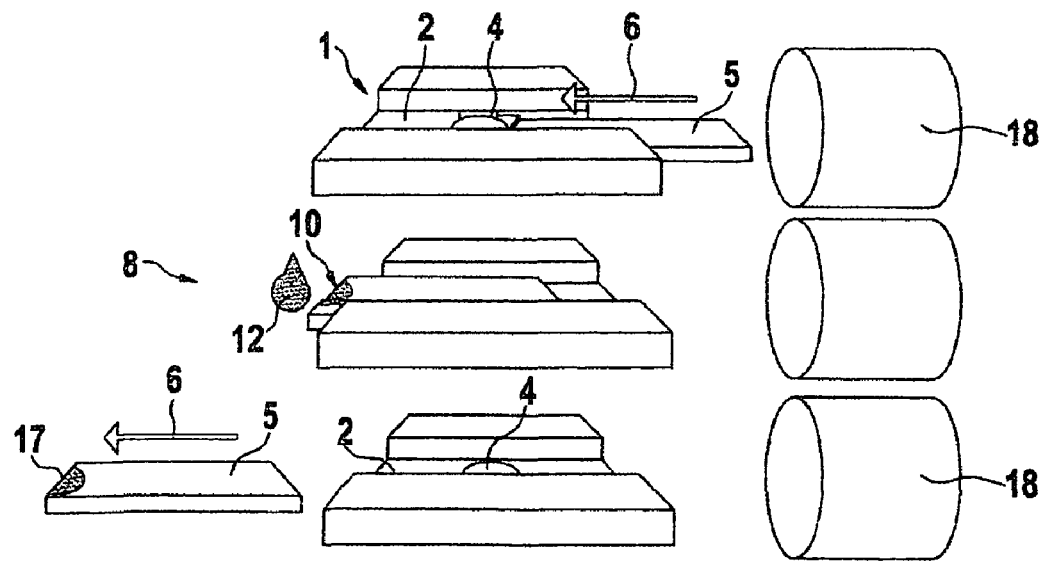
FIG. 2B shows the automatic transport procedure for a test element in an analysis system of the prior art.

FIGS. 2A and 2B demonstrate how test elements in the prior art are handled manually or automatically. FIG. 2A shows the manual handling procedure for a test element in an analysis system of the prior art.

In manually operated analysis systems, the test element 5 is pushed into the analysis system by the user in the introduction direction 6, into the guide element 1 and over the optical window 4. In the sample application position 8, a sample 12 is put onto the sample application site 10 and the measurement is subsequently carried out. After the measurement, the test element 5 is extracted from the analysis system by the operator. The extraction is carried out in the extraction direction 16, which is opposite to the introduction direction 6. The edge 17 of the test element 5, which is wetted with the sample 12, thus never touches the bearing face 2 and the optical window 4, so that staining is avoided. With such an analysis system in the prior art, extraction in the same direction as the introduction direction 6 is not intended and would lead to staining of the bearing face 2, as described with reference to FIG. 1C.

FIG. 2B shows the automatic transport procedure for a test element in an analysis system of the prior art.

In automatically operated analysis systems of the prior art, the test element 5 is pushed from a storage magazine 18 (for example by a plunger, not shown) in the introduction direction 6 into the guide element 1. In the sample application position 8, a sample 12 is applied to the test element 5 at the sample application site 10, and a measurement is carried out. After the measurement, the test element 5 is ejected (for example by the plunger) from the guide element 1 in the same direction as the introduction direction 6. The edge 17 of the test element 5, which is wetted with the sample 12, therefore does not touch the bearing face 2 or the optical window 4, so that staining by the sample 12 is avoided. With such an analysis system in the prior art, extraction of the test element after the measurement in the opposite direction to the introduction direction 6 (for example to put it back into the storage magazine 18) is not intended and would lead to staining of the bearing face 2, as described with reference to FIG. 1C.

Figure 3A:
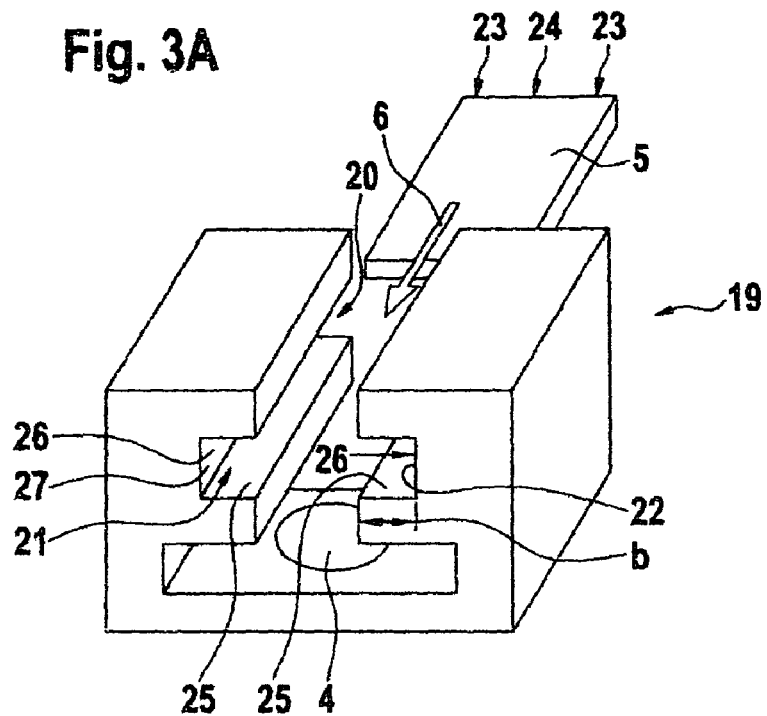
FIG. 3A shows the schematic representation of a detail of an analysis system according to the invention, into which a test element is introduced.

FIG. 3A shows the schematic representation of a detail of an analysis system according to the invention, into which a test element is introduced. The analysis system of the present invention is intended to avoid staining of surfaces in the analysis system by the sample when a test element is being re-magazined after the measurement. The invention furthermore relates to the use of the analysis so that a test element introduced into the guide element will be positioned relative to the analysis unit and the detection unit. Precise positioning of the test field relative to the measuring optics is necessary in order to be able to carry out an exact photometric evaluation, for example. As shown in FIG. 7, the analysis unit 52 and the detection unit 54 are arranged in the analysis system 50. They are arranged e.g. below the optical window 4, which is shown in FIG. 3A.

In an embodiment of the present invention, the test element holder fulfils not only the function of guiding a test element as it is introduced, but also of holding it so that it remains in the measuring position during the measurement. The test element can be introduced reversibly into the test element holder, so that it can be removed from the test element holder after the measurement in the opposite direction to the introduction direction.

The test elements used in the analysis system according to the invention can be test strips in which a liquid sample, in particular blood, urine or interstitial fluid, is transported from the sample application site to the test field by means of capillary action. A channel suitable for capillary liquid transport usually has an entry opening and a ventilation opening. In an embodiment of the present invention, the entry opening is arranged in the vicinity of the sample application site, i.e. in the inner region of the test element. The ventilation opening in the present invention is likewise arranged in the inner region of the test element, so that any sample liquid accidentally emerging from the ventilation opening cannot cause contamination of the test element holder according to the invention.

The test element 5 is introduced into the guide element 20 in the introduction direction 6. The guide element 20 is arranged above the optical window 4 covering the analysis and detection units in the analysis system. A test element 5 introduced into the guide element 20 is at a distance of at least 1 mm from the analysis unit and the detection unit in any position. This distance ensures that no sample material can be drawn from the sample application site 10 of the test element 5 by capillary forces into the gap between the test element 5 and the optical window 4. system according to the invention for analyzing the glucose content in blood on a strip-shaped test element.

The analysis system according to the invention contains an analysis unit and a detection unit for photometric analysis, both of which are arranged (this cannot be seen in FIG. 3A, but can be seen diagrammatically, a non-limiting example of which is shown as analysis unit 52 and detection unit 54 in FIG. 7) below an optical window 4. The analysis system comprises a test element holder 19 into which the test element 5 can be reversibly introduced, and in which it can be positioned relative to the analysis and detection units arranged below the optical window 4. The test element 19 contains a guide element 20 which is suitable for laterally guiding the test element 5. The guide element 20 comprises two mutually opposite grooves 21, 22, into which the test element 5 can be inserted in its outer region 23. The test element 5 is then held and guided in the test element holder 19 only in its outer region 23, and an inner region 24 of the test element 5 introduced into the test element holder 19 remains free. The first and second grooves 21, 22 enclose the outer region 23 of the test element 5 which has been introduced, so that it cannot fall out of the guide element 20 either upwards or downwards (closed guiding). The guide element 20 has support faces 25, on which the test element 5 can rest via bearing faces in its outer region 23, and guide faces 26 along which the test element 5 is guided during transport. During introduction, enough clearance is left around the outer region 23 of the test element 5 so that the test element 5 can be moved with minor force exertion in the guide element 20, and so as to maintain a low level of wear both for the test element 5 and for the guide element 20. The support faces 25 have a width b of between 0.1 mm and 1 mm.

Staining of the analysis system by the sample is avoided in the present invention since the test element is guided and held only in an outer region, and an inner region of the test element introduced into the test element holder remains free. In this context, the term inner region is particularly intended to mean the central part of the two surfaces of the test element. The sample application site, where the sample is put onto the test element, is located in the inner region of the test element so that it does not come in contact with the test element holder and cannot become contaminated by the sample. The guide element is arranged in the analysis system The test element holder 19 may contain a stop (not shown). For example, one end 27 of the grooves 21, 22 may be closed and thus act as a stop. When inserted into the guide element 20, a test element 5 then abuts against the stop as soon as it has reached its sample application position. Such a stop may also be used for test elements 5 which are intended to protrude from the analysis system for the sample application if the test elements 5 have a corresponding shape, in particular if they are tapered in the region of the sample application site, for example in the form of a shoulder or an indentation. The guide element 20 may furthermore contain position switches (not shown) which allow the test element 5 to be positioned accurately.

In the test element holder 19, the guide element 20 may be configured so that the test element 5 is fixed in particular positions by friction or by integrated holding clips or pressure springs (not shown), especially in the sample application or measuring position. Alternatively or in addition, it is possible to fix the test element 5 with the aid of the drive element (plunger, hook, clip, etc.) which is used for transporting the test element 5 automatically into the analysis system according to the invention.

Figure 3B:
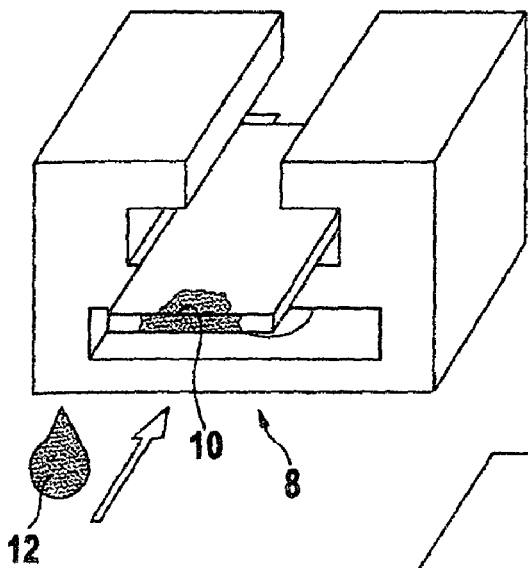
FIG. 3B shows the sample application on a test element in a guide element of an analysis system according to the invention.

FIG. 3B shows the sample application on a test element in a guide element of an analysis system according to the invention.

The test element is located in the sample application position 8, where the sample 12 is put onto the sample application site 10 of the test element 5. The subsequent measurement may likewise take place in the sample application position 8, or it may be carried out in a special measuring position in the analysis system.

Figure 3C:
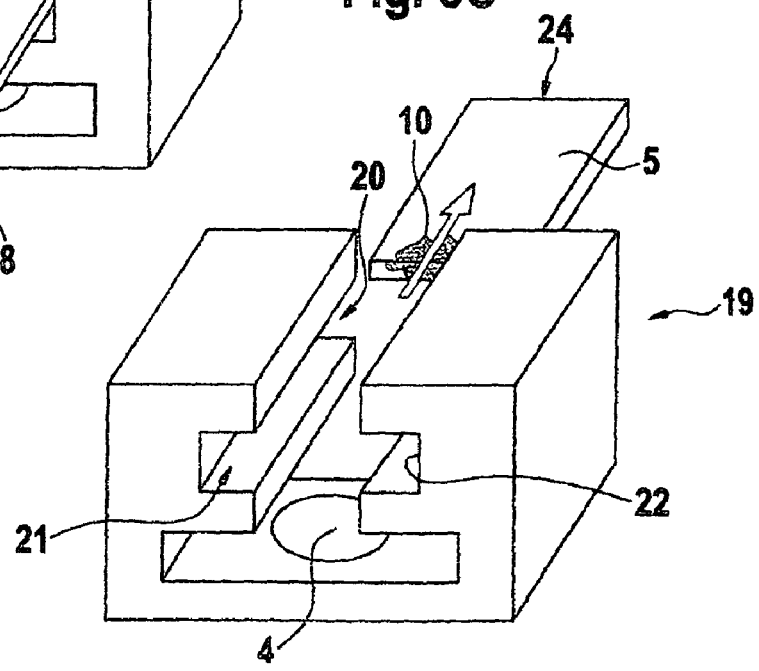
FIG. 3C shows the extraction of a test element after a measurement from a guide element of an analysis system according to the invention.

FIG. 3C shows the extraction of a test element after a measurement from a guide element of an analysis system according to the invention.

After the measurement procedure, the test element 5 is extracted from the test element holder 19 through the guide element 20, and optionally stored (re-magazining) in a storage magazine (not shown). The inner region 24 of the test element 5, which is wetted with the sample material in the vicinity of the sample application site 10, is in this case guided through the test element holder at a secure distance from the optical window 4 and the grooves 21, 22. Surplus sample material, which would cause staining of the interior of the analysis system, cannot therefore become wiped off. The optical window 4 is furthermore not mechanically stressed by the test element as it is being displaced, so that it does not have to be sunk and the design of the analysis system is thereby simplified. The measuring optics present below the optical window 4 are adapted in terms of their distance from the test element 5.

Figure 4:
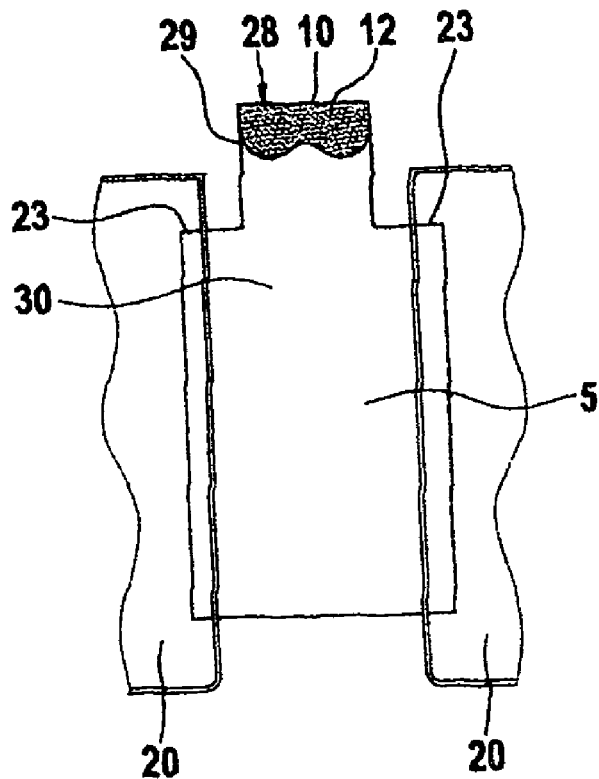
FIG. 4 shows a test element with tapering in the region of the sample application site.

FIG. 4 shows a test element with tapering in the region of the sample application site.

As a further measure against wetting of the test element 5 by the sample 12 over its full width, and against possible concomitant staining of the guide element of the analysis system according to the invention by the sample material, the test element is tapered at one end 28 in the region of the sample application site 10. The tapering 29 has the shape of an indentation which is selected so that with maximum spreading of the sample 12, the wide region 30 of the test element 5 is not wetted by the sample 12. This prevents pollution of the guide element 20, which comes in contact only with the outer region 23 of the test element 5.

Figure 5:
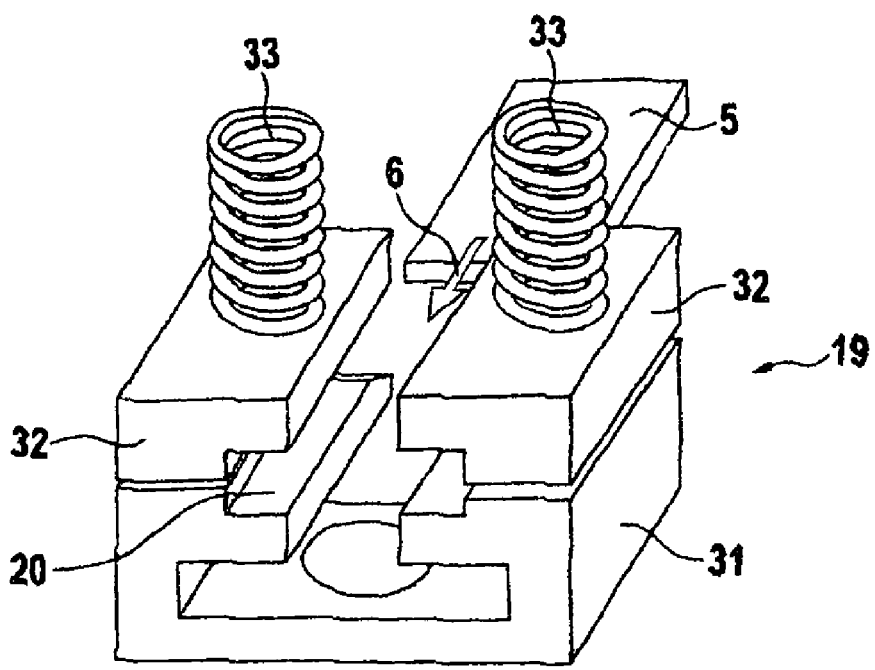
FIG. 5 shows a multi-part test element holder with pressure springs in an analysis system according to the invention.

FIG. 5 shows a multi-part test element holder 19 with pressure springs in an analysis system according to the invention.

The test element holder 19 comprises a lower part 31 and an upper part 32, which lie on top of one another and are laterally secured against displacement. Two pressure springs 33 engage on the upper part 32, and they exert a force on the upper part 32 in the direction of the lower part 31. A test element 5 can be inserted into a guide element 20 in the introduction direction 6, between the lower part 31 and the upper part 32, the two parts 31, 32 are then pressed apart from each other by this test element 5 and the test element 5 fits tightly into the guide element 20. The test element 5 can be additionally fixed in a desired position in the guide element 20 by the pressure of the pressure springs 33.

On the side where a test element 5 is introduced into the test element holder 19 (the rear side not shown in FIG. 5), the test element holder 19 has a ramp- of funnel-shaped introduction opening, through which the test element 5 can be pushed into the guide element 20. This introduction opening facilitates the introduction of a test element 5 which is taller than the inner height of the guide element 20 before introduction of the test element 5.

Figure 6:
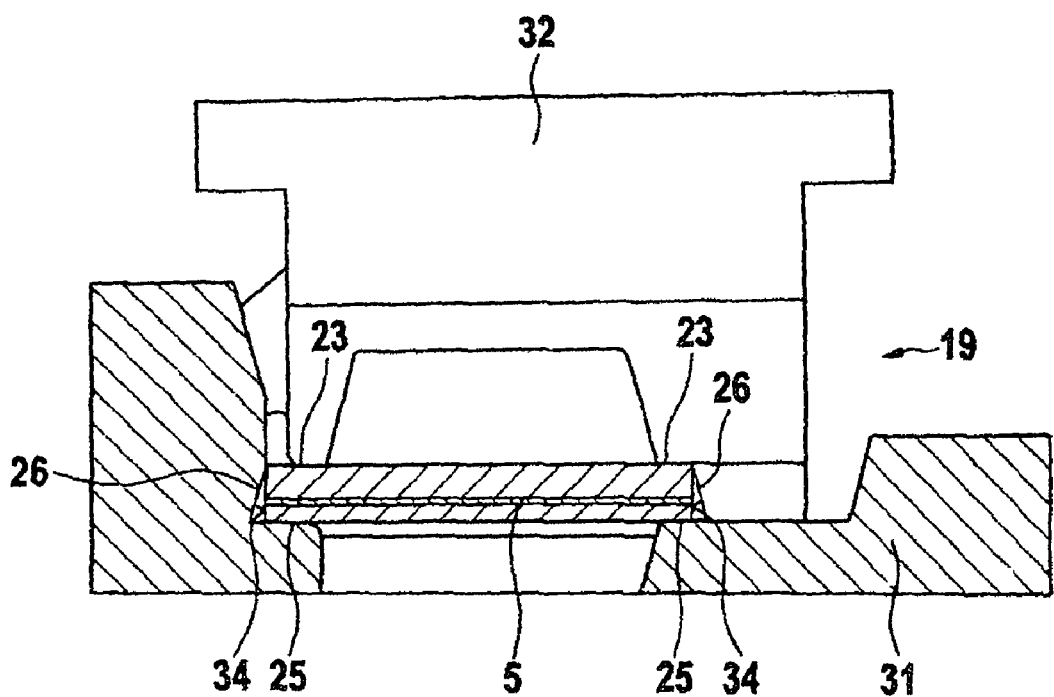
FIG. 6 shows a multi-part test element holder with oblique guide faces.

FIG. 6 shows a multi-part test element holder with oblique guide faces.

The test element holder 19 comprises a lower part 31 and an upper part 32, between which a test element 5 can be inserted into a guide element 20. The guide element 20 has support faces 25, on which the test element 5 rests via bearing faces in its outer region 23, and guide faces 26 along which the side faces 34 of the test element are guided. The guide faces 26 are in this case arranged obliquely with respect to the side faces 34 of the test element 5, in order to avoid staining of the guide faces 26 by the side faces 34 (for example due the adhesive adhering on them).

Having described the invention in detail and by reference to specific embodiments thereof, it will be apparent that modification and variations are possible without departing from the scope of the invention defined in the appended claims. More specifically, although some aspects of the present invention are identified herein, it is contemplated that the present invention is not necessarily limed to these one aspects of the invention.

What is claimed is:

1. Analysis system for analyzing a sample on a test element having an outer region and an inner region, the inner region containing a sample application site, the system comprising:
   an analysis unit for generating a signal as a function of an analyte contained in the sample;
   a detection unit for detecting the signal; and
   a test element holder into which the test element can be reversibly introduced and in which the test element can be positioned relative to the analysis unit and the detection unit, the test element holder comprising a guide element which holds and laterally guides the test element, the guide element defining a gap extending along the length of the guide element, wherein the gap exposes the inner region of the underside of the test element such that the inner region remains free as the test element is removed from the guide element, whereby contamination of the analysis system from sample deposited on the test element is avoided.

2. Analysis system of claim 1, wherein the guide element contains support faces, on which the test element rests via bearing faces in its outer region, and guide faces along which side faces of the test element are guided.

3. Analysis system of claim 2 wherein the guide faces are arranged obliquely with respect to the side faces of the test element.

4. Analysis system of claim 2 wherein the support faces have a width of from 0.1 mm to 1 mm.

5. Analysis system of claim 1 wherein the guide element contains two mutually opposite grooves, into which the test element can be inserted via its outer region.

6. Analysis system of claim 1 wherein the analysis unit and the detection unit are parts of measuring optics which are used to photometrically evaluate the test element.

7. Analysis system of claim 1 wherein the guide element is arranged above the analysis unit and/or the detection unit in the analysis system.

8. Analysis system of claim 1 wherein the guide element is arranged so that a test element introduced into the guide element is at a distance of at least 1 mm from the analysis unit and the detection unit in any position.

9. Analysis system of claim 1 wherein the test element holder has a stop, against which a test element abuts when it is being introduced into the guide element as soon as a defined position of the test element in the test element holder is reached.

10. Analysis system of claim 1 wherein the test element comprises a sample application site at one end in the inner region, the test element being tapered in the region of the sample application site.

11. Analysis system of claim 1 further comprising a storage container for a multiplicity of test elements, into which the test elements are transported back from the test element holder after use.

12. Analysis system of claim 11 further comprising a transport device formed to automatically extract a test element from the storage container, to automatically transport the test element into the test element holder and to automatically transport the test element back into the storage container after use.

13. Analysis system of claim 1 wherein the test element has a test field where the sample is analyzed, which is positioned in the inner region of the test element.

14. Analysis system of claim 13 wherein the test element contains a capillary for delivering the sample to the test field.

15. Analysis system of claim 1 wherein the test element holder is made of at least two parts, with the test element introduced into the test element holder resting in its outer region on a lower part of the test element holder and with a separate upper part of the test element holder resting on the test element in its outer region.

16. Analysis system of claim 15 wherein at least one pressure spring, which exerts a force on the upper part in the direction of the lower part of the test element holder, is arranged on the upper part of the test element holder.

17. Analysis system of claim 1 wherein the guide element has a ramp- or funnel-shaped introduction opening on the side where the test element is introduced into the test element holder.

18. Analysis system of claim 1 wherein the guide element is shaped so that it causes a defined deformation of the test element as it is being introduced into the test element holder, in order to fix it during use.

19. An analysis system for analyzing a sample on a test element having an outer region and an inner region, the inner region containing a sample application site, the system comprising:
   an analysis unit for generating a signal as a function of an analyte contained in the sample; a detection unit for detecting the signal;
   an optical window through which photometric evaluations are conducted; and
   a test element holder into which the test element can be reversibly introduced and in which the test element can be positioned relative to the analysis unit and the detection unit, the test element holder comprising a guide element which holds and laterally guides the test element and maintains the test element spaced from the optical window, wherein the guide element supports a bottom surface of the test element in the outer region of the test element and the guide element does not contact the bottom surface of the test element in the inner region of the test element and the inner region remains spaced from the optical window during the entire removal of the test element from the guide element, whereby contamination of the analysis system from sample deposited on the test element is avoided.

20. Analysis system of claim 19, wherein the guide element contains support faces, on which the test element rests via bearing faces in its outer region, and guide faces along which side faces of the test element are guided.

21. Analysis system of claim 20 wherein the guide faces are arranged obliquely with respect to the side faces of the test element.

22. Analysis system of claim 20 wherein the support faces have a width of from 0.1 mm to 1 mm.

23. Analysis system of claim 19 wherein the guide element contains two mutually opposite grooves, into which the test element can be inserted via its outer region.

24. Analysis system of claim 19 wherein the analysis unit and the detection unit are parts of measuring optics which are used to photometrically evaluate the test element.

25. Analysis system of claim 19 wherein the guide element is arranged above the analysis unit and/or the detection unit in the analysis system.

26. Analysis system of claim 19 wherein the guide element is arranged so that a test element introduced into the guide element is at a distance of at least 1 mm from the analysis unit and the detection unit in any position.

27. Analysis system of claim 19 wherein the test element holder has a stop, against which a test element abuts when it is being introduced into the guide element as soon as a defined position of the test element in the test element holder is reached.

28. Analysis system of claim 19 wherein the test element comprises a sample application site at one end in the inner region, the test element being tapered in the region of the sample application site.

29. Analysis system of claim 19 further comprising a storage container for a multiplicity of test elements, into which the test elements are transported back from the test element holder after use.

30. Analysis system of claim 29 further comprising a transport device formed to automatically extract a test element from the storage container, to automatically transport the test element into the test element holder and to automatically transport the test element back into the storage container after use.

31. Analysis system of claim 19 wherein the test element has a test field where the sample is analyzed, which is positioned in the inner region of the test element.

32. Analysis system of claim 31 wherein the test element contains a capillary for delivering the sample to the test field.

33. Analysis system of claim 19 wherein the test element holder is made of at least two parts, with the test element introduced into the test element holder resting in its outer region on a lower part of the test element holder and with a separate upper part of the test element holder resting on the test element in its outer region.

34. Analysis system of claim 33 wherein at least one pressure spring, which exerts a force on the upper part in the direction of the lower part of the test element holder, is arranged on the upper part of the test element holder.

35. Analysis system of claim 19 wherein the guide element has a ramp- or funnel-shaped introduction opening on the side where the test element is introduced into the test element holder.

36. Analysis system of claim 19 wherein the guide element is shaped so that it causes a defined deformation of the test element as it is being introduced into the test element holder, in order to fix it during use.

* * * * *